United States Patent [19]

Clark et al.

[11] Patent Number: 5,412,102
[45] Date of Patent: May 2, 1995

[54] PROCESSES FOR PREPARING 1-BUTYL-2-[2'-(2H-TETRAZOL-5-YL)BIPHENYL-4-YLMETHYL]-1H-INDOLE-3-CARBOXYLIC ACID

[75] Inventors: Robin D. Clark, Palo Alto; Lawrence E. Fisher, Mountain View; Lee A. Flippin, Woodside; Michael G. Martin, San Francisco; Stephen R. Stabler, Mountain View, all of Calif.

[73] Assignee: Syntex (U.S.A.) Inc., Palo Alto, Calif.

[21] Appl. No.: 250,397

[22] Filed: May 27, 1994

[51] Int. Cl.⁶ .......................................... C07D 257/04
[52] U.S. Cl. .................................................. 548/253
[58] Field of Search ........................................ 548/253

[56] References Cited

U.S. PATENT DOCUMENTS

| 5,093,346 | 3/1992 | Carini et al. | 514/381 |
|---|---|---|---|
| 5,124,335 | 6/1992 | Patchett et al. | 514/300 |
| 5,212,195 | 5/1993 | Clark et al. | 514/381 |

FOREIGN PATENT DOCUMENTS

0516392A2  12/1992  European Pat. Off. .

OTHER PUBLICATIONS

Carini, D. J., et al., "Nonpeptide Angiotensin II Receptor Antagonists: The Discovery of a Series of N-(Biphenylylmethyl) imidazoles as Potent, Orally Active Antihypertensives", J. Med. Chem. (1991), vol. 34, No. 8, pp. 2525–2547.

Primary Examiner—Mary C. Lee
Assistant Examiner—Joseph K. McKane
Attorney, Agent, or Firm—Wayne W. Montgomery

[57] ABSTRACT

The present invention relates to processes for preparing 1-butyl-2-[2'-(2H-tetrazol-5-yl)biphenyl-4-ylmethyl]-1H-indole-3-carboxylic acid and to intermediates useful in such processes. The present invention also relates to a process for deprotecting compounds containing a protected 2H-tetrazolyl group, which process comprises reacting a the protected compound with a Lewis acid in the presence of a thiol.

13 Claims, No Drawings

PROCESSES FOR PREPARING 1-BUTYL-2-[2'-(2H-TETRAZOL-5-YL) BIPHENYL-4-YLMETHYL]-1H-INDOLE-3-CARBOXYLIC ACID

BACKGROUND OF THE INVENTION

1. Field of the Invention

This invention relates to novel processes for preparing 1-butyl-2-[2'-(2H-tetrazol-5-yl)biphenyl-4-ylmethyl]-1H-indole-3-carboxylic acid, an angiotensin II receptor antagonist. This invention also relates to novel intermediates useful in the synthesis of 1-butyl-2-[2'-(2H-tetrazol-5-yl)-biphenyl-4-ylmethyl]-1H-indole-3-carboxylic acid.

2. Description of the Field

The renin-angiotensin system is a fundamental physiological mechanism for regulating blood pressure in meals. Angiotensinogen is secreted into the bloodstream by the liver. Angiotensinogen is then cleaved by the protease renin to yield the decapeptide angiotensin I, which in turn is hydrolyzed by angiotensin converting enzyme (ACE) to the octapeptide angiotensin II.

Angiotensin I is inactive in the cardiovascular system, but angiotensin II has numerous effects. For example, angiotensin II stimulates the adrenal cortex to secrete aldosterone, which causes the kidneys to retain sodium and water, increasing blood pressure. Angiotensin II also causes arteriolar vasoconstriction and facilitates neurotransmission in the sympathetic nervous system. In addition to its effects on the cardiovascular system, angiotensin II contracts gastro-intestinal smooth muscle, produces glycogenolysis, alters renal function and produces various CNS effects. The effects of angiotensin II are mediated by the activation of specific angiotensin II receptors located in smooth muscle, adrenal medulla, brain, liver and kidney tissues. The angiotensin II receptor is presently delineated into two major subtypes (i.e., AT-1 and AT-2 receptor subtypes). Angiotensin II receptor antagonists, particularly those which selectively block AT-1 or AT-2 receptor subtypes, are useful in treating diseases which may be ameliorated by a decrease in the physiological effects of angiotensin II.

Various angiotensin II receptor antagonists are known. See, for example, U.S. Pat. Nos 4,333,943, 4,880,804, 5,053,329, 5,124,335, and European Patents 0 245 637, 0 253 310, and 0 291 969, and also Wong et al. Hypertension 1990, 15, 459, J. Pharmacol. Exp. Ther. 1990, 256, 211, and Chiu etal., Biochem. Biophys. Res. Comm. 1989, 165, 196–203. Substituted indole compounds and derivatives thereof (e.g., 1-butyl-2-[2'-(2H-tetrazol-5-yl)biphenyl-4-yl-methyl]-1H-indole-3-carboxylic acid) are angiotensin II receptor antagonists and are disclosed as such in U.S. Pat. No. 5,212,195 and pending U.S. Pat. application 08/004,869.

The disclosures of these and other documents referred to throughout this application (e.g., in the Pharmacology section of the Detailed Description of the Invention) are incorporated in this application by reference.

SUMMARY OF THE INVENTION

The present invention relates to a process for the preparation of 1-butyl-2- [2'- (2H-tetrazol-5-yl)biphenyl-4-ylmethyl]-1H-indole -3-carboxylic acid which process comprises:

(A)

(i) treating protected 5-phenyl-2H-tetrazole with an organometallic base to give ortho-metalated protected 5-phenyl-2H-tetrazole, (ii) optionally treating the ortho-metalated protected 5-phenyl-2H-tetrazole with a metal halide to give ortho-transmetalated protected 5-phenyl-2H- tetrazole, (iii) reacting the ortho-metalated or ortho-trans-metalated protected 5-phenyl-2H-tetrazole, optionally in the presence of phosphinated nickel or palladium catalyst, with a compound of Formula II:

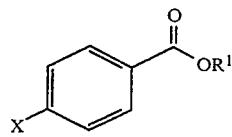

in which X is halo and R' is ($C_{1-4}$) alkyl, to give protected 2'-(2H-tetrazol-5-yl)biphenyl-4-carboxylic acid ($C_{1-4}$) alkyl ester, (iv) reducing the protected 2'-(2H-tetrazol-5-yl)biphenyl-4-carboxylic acid ($C_{1-4}$) alkyl ester to give protected 2'-(2H-tetrazol-5-yl)biphenyl-4-methanol, and (v) halogenating the protected 2'-(2H-tetrazol-5-yl)biphenyl-4-methanol to give protected 4-halomethyl-2'-(2H-tetrazol-5-yl) biphenyl;

(B) reacting the protected 4-halomethyl-2'-(2H-tetrazol-5-yl)biphenyl, optionally in the presence of phosphinated nickel or palladium catalyst, with 2-metalated or 2-transmetalated 1-but-1-yl-1H-indole-3-carboxylic acid to give protected 1-butyl-2-[2'- (2H-tetrazol-5-yl)biphenyl-4-ylmethyl]-1H-indole-3-carboxylic acid; and (C) deprotecting.

A second aspect of this invention relates to a process for the preparation of 1-butyl-2-[2'-(2H-tetrazol-5-yl)biphenyl-4-ylmethyl]-1H-indole-3-carboxylic acid which process comprises:

(A)

(i) treating a compound of Formula IV:

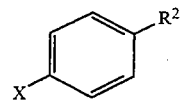

in which X is halo and $R^2$ is 1-isopropyl-2-methylpropyliminomethyl or dimethoxymethyl with an organometallic base to give a corresponding para-metalated intermediate, (ii) optionally treating the para-metalated intermediate with a metal halide to give a para-transmetalated intermediate;

(iii) reacting the para-metalated or para-transmetalated intermediate with a compound of Formula V:

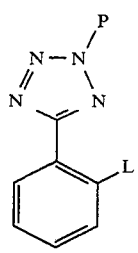

in which L is a leaving group and P is a protective group, and acidifying to give protected 2'-(2H-tetrazol-5-yl)biphenyl-4-carbaldehyde, (iv) reducing the protected 2'- (2H-tetrazol-5-yl)biphenyl-4-carbaldehyde to give protected 2'- (2H-tetrazol-5-yl)biphenyl-4-methanol, and (v) halogenating the protected 2'-(2H-tetrazol-5-yl)biphenyl-4-methanol to give protected 4-halomethyl-2'-(2H- tetrazol-5-yl)biphenyl;

(B) reacting the protected 4-halomethyl-2'-(2H-tetrazol-5-yl)biphenyl, optionally in the presence of phosphinated nickel or palladium catalyst, with 2-metalated or 2-transmetalated 1-but-1-yl-1H-indole-3-carboxylic acid to give protected 1-butyl-2-[2'-(2H-tetrazol-5-yl)biphenyl-4-ylmethyl]-1H-indole-3-carboxylic acid; and (C) deprotecting.

A third aspect of this invention is a compound of Formula III:

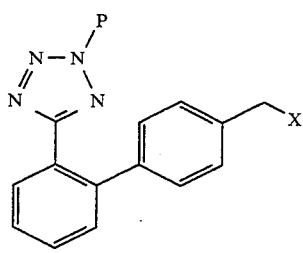

in which P is 1-methyl-1-phenylethyl and X is halo and its use in the preparation of 1-butyl-2-[2'-(2H-tetrazol-5-yl)biphenyl-4-ylmethyl]-1H-indole-3-carboxylic acid.

A fourth aspect of this invention is a compound of Formula VIII:

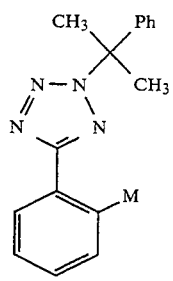

in which Ph is phenyl and M is an alkali metal or a metal halide and its use in the preparation of the compound of Formula III in which P is 1-methyl-1-phenylethyl.

A fifth aspect of the invention is a process for deprotecting compounds containing a protected 2H-tetrazolyl group, which process comprises reacting a the protected compound with a Lewis acid in the presence of a thiol.

DETAILED DESCRIPTION OF THE INVENTION

Definitions:

As used in this application:

"Halo" means bromo, chloro, fluoro or iodo.

"Alkyl" means a straight or branched saturated hydrocarbon radical having from one to the number of carbon atoms designated (e.g., $(C_{1-4})$alkyl includes the radicals methyl, ethyl, prop-1-yl, prop-2-yl, but-1-yl, but-2-yl, 2-methylpropyl and 1,1-dimethylethyl).

"Organometallic base" means a base capable of reacting with an organic compound to give a "metalated" compound of the formula R-Met$^1$ in which Met$^1$ is any monovalent electro positive metal element, typically an alkylmetalic base and preferably an alkyl alkali metal base (e.g., n-butyllithium, n-butylsodium, n-butylpotassium, lithium diisopropylamide (LDA) and the like). A "lithiated" compound means a metalated compound of the formula R-Met$^1$ in which Met$^1$ is -Li.

"Metal halide" means a halide of any multivalent electro positive metal element capable of reacting with a metalated organic compound to give a "transmetalated" compound of the formula R-Met$^2$(X)$_{n-1}$ in which Met$^2$ is the multivalent metal element, X is halo, and n corresponds to the valence of the metal (e.g., -MgI, -ZnCl, NiCl, -ZnBr, -AlCl$_2$, etc.) and includes magnesium chloride, magnesium iodide, magnesium bromide, zinc chloride, zinc iodide, zinc bromide, copper chloride, copper iodide, copper bromide, nickel chloride, nickel iodide, nickel bromide, aluminum chloride, aluminum iodide, aluminum bromide and the like.

"Transmetalation" means the process of reacting a metal halide with a metalated compound to give a transmetalated compound.

"Optional" or "optionally" means that the subsequently described event or circumstance may or may not occur, and that the description includes instances where the event or circumstance occurs and instances in which it does not. For example, "optionally treating the para-metalated intermediate with a metal halide" means that the treatment with metal halide may or may not be carried out in order for the process described to fall within the invention, and the invention includes those processes wherein the treatment occurs and those processes in which it does not.

"Protective group" has the meaning conventionally associated with it in synthetic organic chemistry, i.e., a group which selectively blocks one reactive site in a multifunctional compound such that a chemical reaction can be carried out selectively at another unprotected reactive site and which can be readily removed after the selective reaction is completed. Certain intermediates used in the processes described in this application contain a tetrazol-5-yl moiety in which a reactive nitrogen atom is present. The reactive site in the tetrazol-5-yl moiety can be protected with an acceptable protective group (e.g., 1,1-dimethylethyl, 1-methyl-1-phenylethyl, triphenylmethyl, etc.) which can then be removed by catalytic reduction or chemical cleavage after the selective reaction is completed. The 1-methyl-1-phenylethyl protective group is particularly resistant to cleavage during the selective reaction and is preferred.

"Protective agent" means an agent which will react with a multifunctional compound and create a protective group at reactive nitrogen atoms.

"Protected" in reference to a compound or a group means a derivative of compound or group in which reactive nitrogens are blocked with protective groups.

"Deprotecting" refers to removing any protective groups present after the selective reaction has been carried out.

Certain compounds described in this application contain a tetrazolyl group. The tetrazolyl moiety exists in tautomeric equilibrium between the 1H-tetrazol-5-yl and the 2H-tetrazol-5-yl tautomers. The protected tetrazole group exists as a mixture of the protected 1H-tetrazol-5-yl and 2H-tetrazol-5-yl isomers. Upon removal of the protective group the tetrazolyl group reverts to a tautomeric equilibrium. The compounds which contain the tetrazolyl group or its protected derivative are named, illustrated or otherwise described in this application as the 2H-tetrazolyl tautomer or the protected 2H-tetrazolyl isomer, respectively. However, it is to be understood that the 1H-tetrazolyl tautomers and isomers are encompassed by such names, illustrations and descriptions as well.

The compound of the Formula VII:

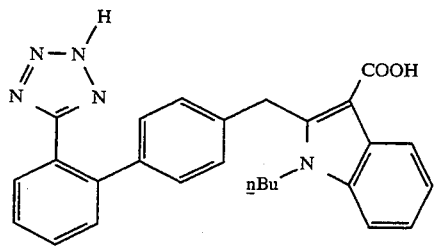

VII is named 1-butyl-2-[2'-(2H-tetrazol-5-yl)biphenyl-4-ylmethyl]-1H-indole-3-carboxylic acid and is described in U.S. Pat. No. 5,212,195 as a angiotensin II receptor antagonist.

The compound of the Formula III in which P is 1-methyl-1-phenylethyl and X is bromo and illustrated by the following formula:

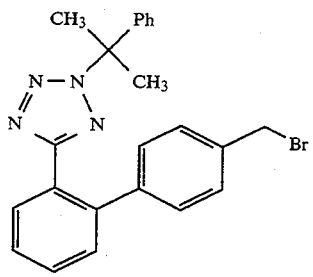

in which Ph is phenyl, is named 4-bromomethyl-2'-[2-(1-methyl-1-phenylethyl)-2H-tetrazol-5-ylbiphenyl and is a useful intermediate in the preparation of 1-butyl-2-[2'-(2H-tetrazol-5-yl)biphenyl-4-ylmethyl]-1H-indole-3-carboxylic acid.

Preferred Embodiments:

While the broadest definition of this invention is set forth in the Summary of the Invention, certain compounds of Formulae III and VIII and procedures for carrying out the processes of this invention are preferred. Preferred compounds of Formula III are those in which P is 1-methyl-1-phenylethyl and X is bromo or iodo, preferably bromo. Preferred compounds of Formula VIII are those in which M is a metal halide, such as -ZnCl, -MgCl or -NiCl, preferably -ZnCl.

A preferred process for the preparation of 1-butyl-2-[2'-(2H-tetrazol-5-yl)biphenyl-4-ylmethyl]-1H-indole-3-carboxylic acid comprises:

(A)

(i) treating 2-(1-methyl-1-phenylethyl)-5-phenyl-2H-tetrazole with n-butyllithium to give ortho-lithiated 2-(1-methyl-1-phenylethyl)-5--phenyl-2H-tetrazole, (ii) treating the ortho-lithiated 2-(1-methyl-1-phenylethyl)-5-phenyl-2H-tetrazole with a metal halide selected from zinc chloride, magnesium chloride or nickel chloride to give ortho-transmetalated 2-(1-methyl-1-phenylethyl)-5-phenyl-2H-tetrazole, (iii) reacting the ortho-transmetalated 2-(1-methyl-1-phenylethyl)-5-phenyl-2H-tetrazole with methyl 4-bromobenzoate in the presence of phosphinated nickel catalyst to give 2'-[2-(1-methyl-1-phenylethyl)-2H-tetrazol-5-yl]biphenyl-4-carboxylic acid methyl ester, (iv) reducing the 2'-[2-(1-methyl-1-phenylethyl) -2H-tetrazol-5-yl]-biphenyl-4-carboxylic acid methyl ester to give 2'- [2-(1-methyl-1-phenylethyl)-2H-tetrazol-5-yl]biphenyl-4-methanol, and (v) brominating the 2'-[2-(1-methyl-1-phenylethyl)-2H-tetrazol-5-yl]- biphenyl-4-methanol to give 4-bromomethyl-2'-[2-(1-methyl-1-phenylethyl)-2H-tetrazol-5-yl]biphenyl;

(B) reacting the 4-bromomethyl-2'-[2-(1-methyl-1-phenylethyl)-2H-tetrazol-5-yl]biphenyl with 2-transmetalated 1-but-1-yl-1H-indole-3-carboxylic acid in the presence of phosphinated palladium catalyst to give 1-butyl-2-[2'-(2-(1-methyl-1-phenylethyl)-2H-tetrazol-5-yl)biphenyl-4-ylmethyl]-1H-indole-3-carboxylic acid; and (C) deprotecting;

preferably wherein the metal halide is zinc chloride, the phosphinated nickel catalyst is bis(triphenylphosphine)-nickel(II)chloride, the 2-transmetalated 1-but-1-yl-1H-indole-3-carboxylic acid is 1-butyl-3-carboxy-1H-indol-2-ylzinc chloride, 1-butyl-3-carboxy-1H-indol-2-ylmagnesium chloride or 1-butyl-3-carboxy-1H-indol-2-ylnickel chloride, preferably 1-butyl-3-carboxy-1H-indol-2-ylzinc chloride, the phosphinated palladium catalyst is tetrakis (triphenylphosphine) palladium (0) and deprotecting comprises reacting the 1-butyl-2-[2'-(2- (1-methyl-1-phenylethyl)-2H-tetrazol-5-yl)biphenyl-4-ylmethyl]-1H-indole-3-carboxylic acid with a Lewis acid in the presence of a thiol.

A preferred process for the preparation of 1-butyl-2-[2'-(2H-tetrazol-5-yl)biphenyl-4-ylmethyl]-1H-indole-3-carboxylic acid comprises:

(A)

(i) treating (4-bromobenzylidene)(1-isopropyl-2-methylpropyl)amine with n-butyllithium to give para-lithiated (benzylidene)(1-isopropyl-2-methylpropyl)amine, (ii) reacting the para-lithiated (benzylidene) (1-isopropyl-2-methylpropyl)amine with 5-(2-methoxyphenyl)-2-(1-methyl-1-phenylethyl)-2H-tetrazole and acidifying to give 2'-[2-(1-methyl-1-phenylethyl)-2H-tetrazol-5-yl]biphenyl-4-carbaldehyde, (iii) reducing the 2'-[2-(1-methyl-1-phenylethyl)-2H-tetrazol-5-yl]-biphenyl-4-carbaldehyde to give 2'- [2-(1-methyl-1-phenylethyl)-2H-tetrazol-5-yl]biphenyl-4-methanol, and (iv) brominating the 2-[2-(1-methyl-1-phenylethyl)-2H-tetrazol-5-yl]-biphenyl-4-methanol to give 4- bromomethyl-2'-[2-(1-methyl-1-phenylethyl)-2H-tetrazol-5-yl]biphenyl;

(B) reacting the 4-bromomethyl-2'- [2-(1-methyl-1-phenylethyl)-2H-tetrazol-5-yl]biphenyl with 2-trans-metalated 1-but-1-yl -1H-indole-3-carboxylic acid in the presence of phosphinated palladium catalyst to give 1-butyl-2- 8 2'- (2-(1-methyl-1-phenylethyl)-2H-tetrazol-5-yl)biphenyl-4ylmethyl]-1H-indole-3-carboxylic acid; and (C) deprotecting;

preferably wherein the 2- transmetalated 1-but-1-yl-1H-indole-3-carboxylic acid is 1-butyl-3-carboxy-1H-indol-2-ylzinc chloride, 1-butyl-3-carboxy-1H-indol-2-ylmagnesium chloride or 1-butyl-3-carboxy-1H-indol-2-ylnickel chloride, preferably 1-butyl-3-carboxy-1H-indol-2-ylzinc chloride, and the phosphinated palladium catalyst is tetrakis (triphenylphosphine)palladium(0).

A preferred process for deprotecting a compound containing a protected 2H-tetrazolyl group is that in which the Lewis acid is boron trifluoride etherate, tin (IV) chloride, titanium (IV) chloride, titanium (III ) chloride, zinc chloride or selenium(IV) chloride, preferably boron trifluoride etherate, and the thiol is methyl thioglycolate, pentaerythritol tetrakis(2-mercaptoacetate), ($C_{1-4}$) alkanethiol, arylthiol, 2-mercaptoacetic acid or ($C_{1-4}$) alkyl 2-mercaptoacetate, preferably methyl thioglycolate or pentaerythritol tetrakis (2-mercaptoacetate).

Process for preparing 1-butyl-2-[2'-(2H-tetrazol-5-yl)biphenyl-4-ylmethyl]-1H-indole-3-carboxylic acid:

While the present invention has been described with respect to specific embodiments thereof, it will be understood by those skilled in the art that various changes may be made and equivalents may be substituted without departing from the true spirit and scope of the invention. All such modifications are intended to be within the scope of the claims appended to this application.

The processes of the invention are depicted by the following reaction scheme:

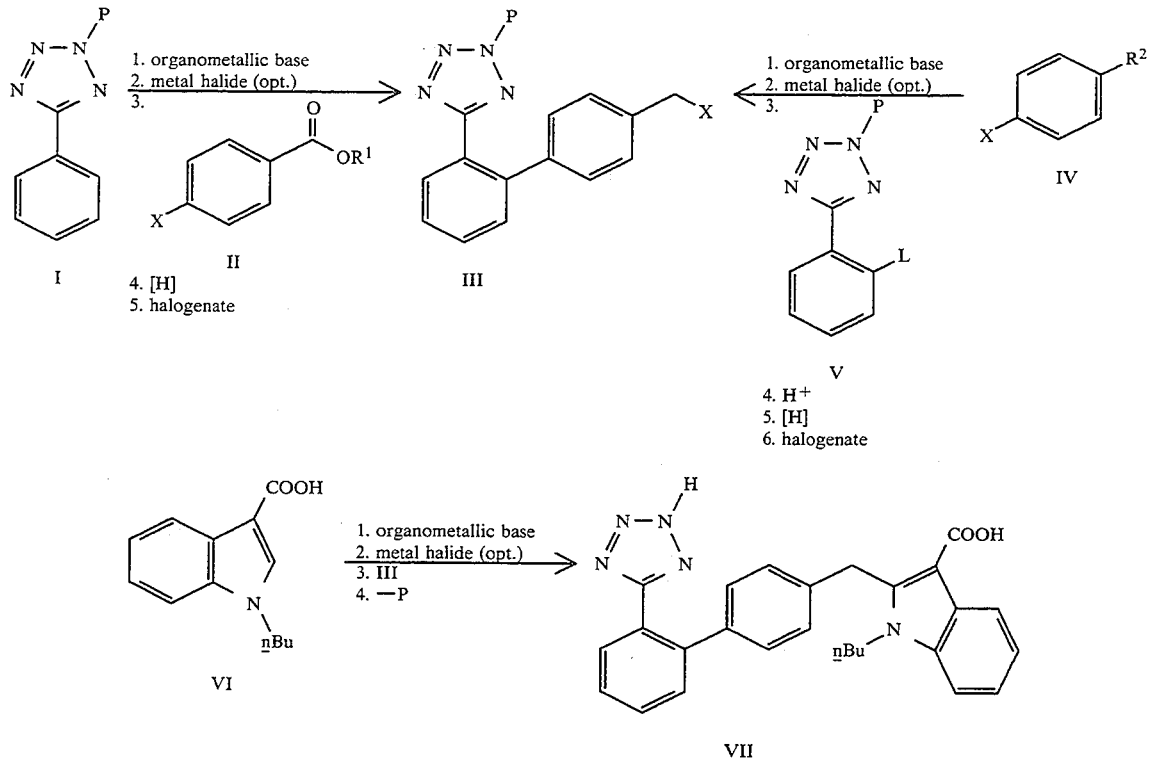

in which L, P, X, $R^1$ and $R^2$ are as defined in the Summary of the Invention.

1-Butyl -2- 8 2'- (2H-tetrazol-5-yl)biphenyl-4-ylmethyl]-1-indole-3-carboxylic acid (Formula VII) can be prepared by reacting 2-metalated or 2-transmetalated 1-but-1-yl-1H-indole-3-carboxylic acid with protected 4-halomethyl-2'- (2H-tetrazol-5-yl)biphenyl (Formula III) to give protected 1-butyl-2-{2'- 2-(2H-tetrazol-5-yl)biphenyl-4-ylmethyl}-1H-indole-3-carboxylic acid and then deprotecting. The 2-metalated 1-but-1-yl-1H-indole-3-carboxylic acid is prepared by cooling a solution of the 1-but-1-yl-1H-indole-3-carboxylic acid (Formula VI) in a suitable solvent, preferably an ether (e.g., tetrahydrofuran (THF), diethyl ether, monoglyme, diglyme, preferably THF), to between −70° and 10° C., typically to between ±35° to 5° C. and preferably to approximately 0° C., adding an organometallic base, typically an alkylmetallic base and preferably an alkyl alkali metal base (e.g., n-butyllithium, n-butylsodium, n-butylpotassium, lithium diisopropylamide (LDA), etc., preferably n-butyllithium), at a rate such that the reaction temperature remains below 15° C., preferably below 5° C., and then allowing the reaction to proceed at −70° to 15° C., typically at −10° to 10° C. and preferably at approximately 0° C., for 10 minutes to 5 hours.

The transmetalation and/or the reaction with the protected 4-halomethyl-2'-(2H-tetrazol-5-yl)biphenyl is carried out by cooling the solution containing the 2-metalated 1-but-1-yl-1H-indole-3-carboxylic acid to between −60° and 15° C., typically to between −45° and 10° C. and preferably to approximately 0° C., adding a suitable metal halide (e.g., magnesium chloride, zinc chloride, nickel chloride, etc, preferably zinc chloride) and/or the protected 4-halomethyl-2'-(2H-tetrazol-5-yl)biphenyl and then allowing the reaction to proceed at −10° to 30° C., typically at 15° to 25° C. and preferably at approximately 22° C., for 0 minutes to 48 hours. Preferably the reaction is carried out in the presence of a suitable catalyst, preferably a phosphinated nickel or palladium catalyst (e.g., tetrakis(triphenylphosphine)nickel(0), tetrakis(triphenylphosphine)palladium(0), bis(triphenylphosphine)nickel(II)chloride, bis(triphenylphosphine)palladium(II)chloride, etc., preferably tetrakis(triphenylphosphine)palladium(O)). The preparation of protected 1-butyl-2-[2'- (2H-tetrazol-5-yl)-biphenyl-4-ylmethyl]-1H-indole-3-carboxylic acid, wherein the protective group is 1-methyl-1-phenylethyl, is described in Example 14.

Deprotection is effected by any means which removes the protective group from the 2H-tetrazol-5-yl group to give the desired unprotected product in reasonable yield. A detailed description of the techniques applicable to protective groups and their removal can be found in T. W. Greene, Protective Groups in Organic Synthesis, John Wiley & Sons, Inc. 1981. This application describes a novel and convenient method for deprotecting a protected 2H-tetrazol-5-yl group, particularly wherein the protective group is 1-methyl-1-phenylethyl-2H-tetrazol-5-yl.

This novel deprotecting method comprises reacting the protected derivative with 1 to 10 molar equivalents, typically 2 to 6 molar equivalents and preferably approximately 4 molar equivalents, of a Lewis acid (e.g., boron trifluoride etherate, tin(IV)chloride, titanium(IV)chloride, titanium(III)chloride, zinc chloride or selenium(IV)chloride, etc., preferably boron trifluoride etherate) in the presence of 1 to 5 molar equivalents, typically 2 to 4 molar equivalents and preferably approximately 3 molar equivalents, of a thiol (e.g., ($C_{1-4}$)alkanethiols such as methanethiol, ethanethiol, 1-propanethiol, 2-propanethiol and the like, arylthiols such as thiophenol and the like, 2-mercaptoacetic acid, ($C_{1-4}$)alkyl 2-mercaptoacetates such as methyl thioglycolate, methyl 2-mercaptoacetate, ethyl 2-mercaptoacetate and the like, pentaerythritol tetrakis(2-mercaptoacetate), etc., preferably methyl thioglycolate or pentaerythritol tetrakis(2-mercaptoacetate)) in a suitable nitrile or ether solvent (e.g., acetonitrile, THF, diethylether, etc., preferably acetonitrile). The reaction is carried out at −10° to 50° C., typically at 10° to 40° C. and preferably at approximately 25° C., for 0.5 to 15 hours. This deprotecting process is particularly useful for deprotecting protected 1-butyl-2-[2'-(2H-tetrazol-5-yl)biphenyl-4-ylmethyl]-1H-indole-3-carboxylic acid. The deprotection of 1-butyl-2-{2'-[2-(1-methyl-1-phenylethyl)-2H-tetrazol-5-yl]biphenyl-4-ylmethyl}-1H-indole-3-carboxylic acid is described in Example 15.

1-But-1-yl-1H-indole-3-carboxylic acid can be prepared by treating 1H-indole-3-carboxylic acid with an alkali metal hydride (e.g., lithium hydride, potassium hydride, sodium hydride, etc.) in a suitable solvent (e.g., acetamide, dimethylsulfoxide (DMSO), dimethylformamide (DMF), preferably DMF) and then reacting with n-butyl halide, preferably n-butyl bromide. The procedure is carried out by cooling a solution of the alkali metal hydride (1 to 1.5 molar equivalents) to between −20° and 10° C., typically to between −10° and 5° C. and preferably to approximately 0° C., and then slowly adding the 1H-indole-3-carboxylic acid. The reaction mixture is then stirred for 10 minutes to 4 hours, cooled to between −2° and 10° C., typically to between −2° to 5° C. and preferably to approximately 0° C. and then the n-butyl halide (1 to 1.5 molar equivalents) is added. The preparation of 1-but-1-yl-1H-indole-3-carboxylic acid is described in Example 13.

The protected 4-halomethyl-2'-(2H-tetrazol-5-yl)biphenyl can be prepared by halogenating protected 2'-(2H-tetrazol-5-yl)biphenyl-4-methanol. The halogenation can be effected with a appropriate halogenating agent (e.g., N-bromosuccinimide, N-iodosuccinimide, N-chlorosuccinimide, etc., preferably N-bromosuccinimide) in a suitable solvent, preferably an ether (e.g., THF, diethylether, monoglyme, etc.), in the presence of triphenylphosphine at −10° C. to 30° C., typically at 15° to 30° C. and preferably at approximately 25° C., and requires 1 to 10 hours. The preparation of 4-bromomethyl-2'-[2-(1-methyl-1-phenylethyl)-2H-tetrazol-5-yl]biphenyl is described in Example 12.

The protected 2'-(2H-tetrazol-5-yl)biphenyl-4-methanol can be prepared by reducing protected 2'-(2H-tetrazol-5-yl)biphenyl-4-carboxylic acid ($C_{1-4}$)alkyl ester. The reduction can be effected with a chemical reducing agent, preferably lithium aluminum hydride, in a suitable solvent, preferably an ether (e.g., THF, diethylether, etc.), at −15° C. to 25° C., typically at −10° to 10° C. and preferably at approximately 0° C., and requires 1 to 6 hours. The reduction of 2,-[2-(1-methyl-1-phenylethyl)-2H-tetrazol-5-yl]biphenyl-4-carboxylic acid methyl ester is described in Example 10.

The protected 2'-(2H-tetrazol-5-yl)biphenyl-4-carboxylic acid ($C_{1-4}$)alkyl ester can be prepared by reacting protected ortho-metalated or ortho-transmetalated 5-phenyl-2H-tetrazole with a ($C_{1-4}$) alkyl 4-halobenzoate (Formula II), preferably methyl 4-bromobenzoate. Protected ortho-metalated 5-phenyl-2H-tetrazole is prepared by metalation of protected 5-phenyl-2H-tetrazole (Formula I). The metalation is carried out by cooling a solution of the protected 5-phenyl-2H-tetrazole in a suitable solvent, preferably an ether (e.g., THF, diethyl ether, monoglyme, diglyme, preferably THF), to between −70° and 0° C., typically to −25° to −5° C. and preferably to approximately −15° C., adding an organometallic base, typically an alkylmetallic base and preferably an alkyl alkali metal base (e.g., n-butyllithium, n-butylsodium, n-butylpotassium, lithium diisopropylamide (LDA), etc., preferably n-butyllithium) at a rate such that the reaction temperature remains below 0° C., preferably below −10° C., and then allowing the reaction to proceed at −10° to 35° C., typically at −10° to 10° C. and preferably at approximately 0° C., for 45 minutes to 48 hours.

The protected ortho-transmetalated 5-phenyl-2H-tetrazole is prepared by transmetalation of the corresponding protected ortho-metalated 5-phenyl-2H-tetrazole. The transmetalation of the ortho-metalated 5-phenyl-2H-tetrazole and/or the reaction with the ($C_{1-4}$)alkyl 4-halobenzoate is carried out by cooling the solution containing the metalated tetrazole to between −15° and 0° C., typically to between −15° to −5° and preferably to approximately −10° C., adding a suitable metal halide (e.g., magnesium chloride, zinc chloride, nickel chloride, etc, preferably zinc chloride) and/or the ($C_{1-4}$)alkyl 4-halobenzoate and then allowing the reaction to proceed at −10° to 35° C., typically at 10° to 30° C. and preferably at approximately 22° C., for 45 minutes to 48 hours. Preferably the reaction with the ($C_{1-4}$)alkyl 4-halobenzoate is carried out in the presence of a suitable catalyst, preferably a phosphinated nickel or palladium catalyst (e.g., tetrakis(triphenylphosphine)nickel(0), tetrakis triphenylphosphine)palladium(O), bis(triphenylphosphine)nickel(II)chloride, bis(triphenylphosphine) palladium(II)chloride, etc., preferably bis(triphenylphosphine)nickel (II)chloride). The preparation of 2'-[2-(1-methyl-1-phenylethyl)-2H-tetrazol-5-yl]biphenyl-4-carboxylic acid methyl ester is described in Example 3.

The protected 5-phenyl-2H-tetrazole can be prepared by reacting 5-phenyl-2H-tetrazole with 1 to 2 molar equivalents a suitable protective agent (e.g., 2-methyl-2-propanol, 2-phenyl-2-propanol, α-methylstyrene, triphenylmethyl chloride, etc., preferably α-methylstyrene) in a suitable solvent, preferably acetic solvent (e.g., trifluoroacetic acid, methanesulfonic acid, etc., preferably trifluoroacetic acid) at 5° to 100° C., typically at 20° to 50° C. and preferably at approximately 30° C., for 8 to 24 hours. The preparation of 5-phenyl-2-(1-methyl-1-phenylethyl)-2H-tetrazole is described in Example 2. The $(C_{1-4})$alkyl 4-halobenzoate can be prepared by reacting 4-halobenzoic acid, preferably 4-bromobenzoic acid with a $(C_{1-4})$ alcohol, preferably methanol, in the presence of sulfuric acid at 25° to 65° C., typically at 55° to 65° C. and preferably at approximately 65° C. for 1 to 15 hours. The preparation of methyl 4-bromobenzoate is describe in Example 1.

Alternatively, the protected 2'-(2H-tetrazol-5-yl)biphenyl-4-methanol can be prepared by reducing protected 2'-(2H-tetrazol-5-yl)biphenyl-4-carbaldehyde. The reduction of the protected carbaldehyde can be effected with a chemical reducing agent, preferably sodium borohydride in a suitable solvent, preferably an alcohol (e.g., ethanol) at 0° to 30° C., typically 20° to 30° C. and preferably at approximately 25° C., and requires 10 minutes to 2 hours. The reduction of 2'-[2-(1-methyl-1-phenylethyl)-2H-tetrazol-5-yl]biphenyl-4-carbaldehyde is described in Example 11.

The protected 2'-(2H-tetrazol-5-yl)biphenyl-4-carbaldehyde can be prepared by reacting an appropriate para-metalated or para-transmetalated intermediate with a compound of Formula V and then acidifying. The para-metalated intermediate is prepared by cooling a solution of a compound of Formula IV in a suitable solvent, preferably an ether (e.g., THF, diethyl ether, dioxane, preferably THF), to between −75° and 25° C., typically to between −50° to −70° C. and preferably approximately −60° C., and then adding to the solution an organometallic base, typically an alkylmetallic base and preferably an alkyl alkali metal base (e.g., n-butyllithium, n-butylsodium, n-butylpotassium, lithium diisopropylamide (LDA), etc., preferably n-butyllithium) at a rate such that the reaction temperature remains below 0° C., preferably below −40° C., and then allowing the reaction to proceed at −40° to 25° C., typically at −10° to 10° C. and preferably at approximately 0° C., for 15 minutes to 2 hours.

The transmetalation and/or the reaction with the compound of Formula V is carried out by cooling the solution containing a para-metalated intermediate to between −78° and 0° C., typically to between −20° to 0° C. and preferably to approximately 0° C., and then adding a suitable metal halide (e.g., magnesium chloride, zinc chloride, zirconium chloride, etc, preferably zinc chloride) and/or compound of Formula V and then allowing the reaction to proceed at 0° to 30° C., typically at 15° to 30° and preferably at approximately 22° C., for 15 minutes to 2 hours. The acidification can be carried out with dilute hydrochloric acid in a suitable solvent (e.g., 1:1 water/THF, methanol, etc.) at 25° to 50° C. and requires 15 minutes to 4 hours. The preparation of protected 2'-(2H-tetrazol-5-yl)biphenyl-4-carbaldehyde is described in Examples 7 and 8.

Compounds of Formula IV in which $R^2$ is 1-isopropyl-2-methylpropyliminomethyl can be prepared by reacting an appropriate halogenated benzaldehyde with 2,4-dimethylpent-3-ylamine in a suitable solvent, preferably toluene, at reflux for 1 to 14 hours. Compounds of Formula IV in which $R^2$ is dimethoxymethyl can be prepared by reacting an appropriate halogenated benzaldehyde with trimethyl orthoformate in a suitable solvent, preferably methanol, at reflux for 1 to 14 hours. The preparation of a compound of Formula IV in which $R^2$ is either 1-isopropyl-2-methylpropyliminomethyl or dimethoxymethyl is described in Examples 4 and 5, respectively.

The compounds of Formula V can be prepared from the appropriate 2-substituted 1-cyanobenzene. For example a compound of Formula V in which L is methoxy can be prepared by reacting 1-cyano-2-methoxybenzene with tributyltin azide to give 5-(2-methoxyphenyl)-2H-tetrazole and then creating an appropriate protective group. The reaction with the azide is carried out in a suitable solvent, preferably xylene, at reflux and requires 4 to 24 hours. The protective group can be created by reacting the tetrazole with 1 to 2 molar equivalents of a suitable protective agent (e.g. 2-methyl-2-propanol, 2-phenyl-2-propanol, α-methylstyrene, triphenylmethyl chloride, etc.) in a suitable acidic solvent (e.g., trifluoroacetic acid, trichloroacetic acid in methylene chloride, etc.) at 0° to 30° C., typically at 20° to 30° C. and preferably at approximately 25° C., for 1 to 14 hours. The preparation of a compound of Formula V is described in Example 6.

EXAMPLE 1

Methyl 4-Bromobenzoate

The following is the preparation of a compound of Formula II in which X is bromo and $R^1$ is methyl.

4-Bromobenzoic acid (9.98 kg, 48 mol) was suspended in 40 kg of methanol. Sulfuric acid (2 kg, 20 mol) was added and the mixture was heated under reflux for approximately 5 hours. The mixture was cooled over 10 hours to −10° C. and allowed to stand for 5 hours giving a crystalline product. The product was isolated by filtration and the filter cake was washed with methanol (2×3 L). Drying gave methyl 4-bromobenzoate (9.97 kg, 42 mol), m.p. 78°–78.7° C.

EXAMPLE 2

5-Phenyl-2-(1-methyl-1-phenylethyl)-2H-tetrazole

The following is the preparation of a compound of Formula I in which P is 1-methyl-1-phenylethyl.

5-Phenyl-2H-tetrazole (1.0 kg, 6.8 mol) was dissolved in 2.0 L of trifluoroacetic acid. The mixture was allowed to cool to approximately 25° C. and α-methylstyrene (7.58 M, 900 mL, 6.8 mol) was added at a rate such that the reaction temperature remained below 35° C. The reaction mixture was stirred at room temperature for 3 hours and then transfered into approximately 12 L of 0% potassium hydroxide. The mixture was cooled in an ice bath and then 4 L of hexane was added. The hexane layer was separated and combined with 6 L of water. The mixture was stirred and then combined with 1 L of ethyl acetate. The hexane layer was separated, filtered and the filter cake washed with 0.5 L of ethyl acetate.

The filtrate was concentrated to a volume of 2 L. The residue was cooled and a crystalline product was obtained. The residue was filtered, the filter cake washed with 3×200 mL of hexanes and the isolated product dried. The filtrate was concentrated to a volume of 1 L. The residue was cooled and a crystalline product was obtained. The residue was filtered, the filter cake washed with 2×100 mL of hexanes and the isolated product dried. The filtrate was concentrated to 0.25 L of oil and approximately 1 g of isolated dried product was added as seeds. The oil residue was cooled and a crystalline product was obtained. The residue was filtered, the filter cake washed with 2×100 mL of hexanes and the isolated product dried. Combining the dry, isolated product gave 5-phenyl-2-(1-methyl-1-phenylethyl)-2H-tetrazole (1.48 kg, 5.6 mol), m.p. 44°–46° C.

EXAMPLE 3

2'-[2-(1-Methyl-1-phenylethyl)-2H-tetrazol-5-yl]biphenyl-4-carboxylic acid methyl ester The following is the preparation of protected 2'-(2H-tetrazol-5-yl)-biphenyl-4-carboxylic acid $(C_{1-4})$alkyl ester wherein the protective group is 1-methyl-1-phenylethyl and the $(C_{1-4})$alkyl is methyl.

5-phenyl-2-(1-methyl-1-phenylethyl)-2H-tetrazole (66.0 g, 0.25 mol), prepared as in Example 2, was dissolved in 140 mL of THF. The mixture was cooled to −10° C. and n-butyllithium (1.6 M in hexanes, 160 mL, 0.26 mol) was added at a rate such that the reaction temperature remained below 0° C. The mixture was allowed to stand at 0° C. for approximately 1 hour and then was added to a solution of zinc chloride (1 M, 250 mL, 0.25 mol) in ether at a rate such that the reaction temperature remained below 10° C. The mixture was cooled to 0° C. and methyl 4-bromobenzoate (50.0 g, 0.23 mmol), prepared as in Example 1, in 250 mL of THF was added along with a suspension of bis(triphenylphosphine)nickel(II)chloride (8.2 g) and methyl magnesium chloride (3 M in THF, 10 mL, 30 mmol) in 110 mL THF and the mixture was stirred for 3 hours.

The mixture was allowed to stand under nitrogen for approximately 36 hours and then 60 mL of concentrated hydrochloric acid in 400 mL of ice-water was added. The product was extracted with 200 mL of ethyl acetate and the organic layer was washed twice with 400 mL of water. Sulfaflox (10 g) was added to the organic layer and the mixture was filtered through a layer of sulfaflex. The layer of sulfaflox was rinsed with ethyl acetate and the solvents were evaporated giving a crystalline product. The residue was mixed with 200 mL of methanol and the resultant slurry was cooled in an ice bath. The product was isolated by filtration and the filter cake washed with 50 mL of cold methanol. Drying gave gave 2'-[2-(1-methyl-1-phenylethyl)-2H-tetrazol-5-yl]biphenyl-4-carboxylic acid methyl ester (78.69 g, 0.197 mol), m.p. 97°–98° C.

EXAMPLE 4

(4-Bromobenzylidene)(1-isopropyl-2-methylpropyl)amine

The following is the preparation of a compound of Formula IV in which X is bromo and $R^2$ is 1-isopropyl-2-methylpropyliminomethyl.

A mixture of 4-bromobenzaldehyde (7.3 g, 40.0 mmol), 2,4-dimethylpent-3-ylamine (4.8 g, 41.4 mmol), and para-toluenesulfonic acid (0.05 g, 0.29 mmol) in 125 mL of toluene was heated under reflux while water was removed with a Dean-Stark trap. The toluene then was removed under vacuum and distillation of the remaining residue gave (4-bromobenzylidene)(1-isopropyl-2-methylpropyl)amine (10.71 g) as a clear colorless oil.

EXAMPLE 5

1-Bromo-4-(dimethoxymethyl)benzene

The following is the preparation of a compound of Formula IV in which X is bromo and $R^2$ is dimethoxymethyl.

A mixture of 4-bromobenzaldehyde (21.9 g, 120 mmol), methyl orthoformate (50 mL, 457 mmol), and para-toluenesulfonic acid (0.05 g, 0.29 mmol) in 100 mL of methanol was heated under reflux for 5 hours. The solvent was removed under vacuum and distillation of the remaining residue gave 1-bromo-4-(dimethoxymethyl)benzene (2.24 g, 9.7 mmol) as a clear colorless oil.

EXAMPLE 6

1-(1,1-Dimethylethyl)-5-(2-methoxyphenyl)-2H-tetrazole

The following is the preparation of a compound of Formula V in which L is methoxy and P is 1,1-dimethylethyl.

Step (a)

A mixture of 1-cyano-2-methoxybenzene (1.02 g, 7.7 mmol) and tributyltin azide (3.4 g, 10.0 mmol) in 3.0 mL of xylene was heated under reflux for hours. The reaction mixture then was cooled and diluted with diethyl ether. Anhydrous hydrochloric acid was bubbled into the mixture and a white precipitate formed. The precipitate was collected by suction filtration and washed repeatedly with diethyl ether. Drying gave 5-(2-methoxyphenyl)-2H-tetrazole (1.33 g, 7.55 mmol).

Step (b)

A mixture of 5-(2-methoxyphenyl)-2H-tetrazole (0.83 g, 4.71 mmol), 2-methyl-2-propanol (0.7 g, 9.4 mmol), and sulfuric acid (0.24 g, 2.4 mmol) in 4.6 mL of TFA was stirred under nitrogen at room temperature for 16 hours. The reaction mixture then was diluted with ethyl acetate, poured into 2 M potassium hydroxide, and extracted with ethyl acetate. The ethyl acetate layer was washed with water, dried over magnesium sulfate and concentrated. Purification of the residue by column chromatography on silica gel (elution: 10% ethyl acetate/hexane) gave 1-(1,1-dimethylethyl)-5-(2-methoxyphenyl)-2H-tetrazole (0.5102 g, 1.67 mmol), as an oil.

Proceeding as in Example 6 but replacing 2-methyl-2-propanol with 2-phenyl-2-propanol gave 5-(2-methoxyphenyl)-1-(1-methyl-1-phenylethyl)-2H-tetrazole as an oil.

EXAMPLE 7

5-(2-methoxyphenyl)-1-triphenylmethyl-2H-tetrazole

The following is the preparation of a compound of Formula V in which L is methoxy and P is triphenylmethyl.

A mixture of 5-(2-methoxyphenyl)-2H-tetrazole (1.0 g, 5.7 mmol), prepared as in Example 6, Step (a), and sodium hydride (0.8 g) in 20 mL of 1-methyl-2-pyrrolidinone was stirred under hydrogen and triphenylmethyl chloride (1.5 g, 5.4 mmol) was added. The mixture was stirred for 2 hours and then poured into water. The mixture was filtered and the filtered residue was dissolved in methylene chloride. Purification of the residue by column chromatography on silica gel (elution: 20% ethyl acetate) gave 5-(2-methoxyphenyl)-1- triphenylmethyl-2H-tetrazole (1.2 g, 2.9) m.p. 165°-170° C.

EXAMPLE 8

2'-[2-(1,1-dimethylethyl)-2H-tetrazol-5-yl)-biphenyl-4-carbaldehyde

The following is the preparation of a protected 2'-(2H-tetrazol-5-yl)-biphenyl-4-carbaldehyde wherein the protective group is 1,1-dimethylethyl.

A solution of (4-bromobenzylidene)(1-isopropyl-2-methylpropyl)amine (1.41 g, 5.0 mmol), prepared as in Example 4, in 5.0 mL of dry diethyl ether was cooled to −55° C. and n-butyllithium (3.2 mL, 1.6 M in hexane, 5.0 mmol) was added over 5 minutes. The mixture was allowed to warm to −40° C. and held at that temperature for 15 minutes. The mixture was then allowed to warm to −15° C. over 10 minutes and 1-(1,1-dimethylethyl)-5-(2-methoxyphenyl)-2H-tetrazole (0.683 g, 0.294 mol), prepared as in Example 6, in 2.0 mL of diethyl ether was added rapidly. The mixture was allowed to warm to 22° C., let stand for 45 minutes and 50 mL of saturated ammonium chloride was added. The mixture was diluted with 150 mL of diethyl ether and washed twice with 150 mL of saturated ammonium chloride and once with 100 mL of water. The diethyl ether layer was dried over magnesium sulfate and concentrated. The residue was dissolved in 0.5 mL of 12.0 M hydrochloric acid, 20 mL of THF and 20 mL of water and the solution was heated under reflux on a steam bath for 30 minutes. The reaction mixture was cooled and extracted three times with 100 mL of diethyl ether. The combined diethyl ether layers were dried over magnesium sulfate, filtered and concentrated. Purification of the residue by column chromatography on silica gel (elution: 10% ethyl acetate/hexane) gave 2'-[2-(1,1-dimethylethyl)-2H-tetrazol-5-yl]biphenyl-4-carbaldehyde (0.5102 g, 1.67 mmol), as an oil.

Proceeding as in Example 8 but replacing 1-(1,1-dimethylethyl)-5-(2-methoxyphenyl)-1H-tetrazole with 5-(2-methoxyphenyl)-1-(1-methyl-1-phenylethyl)-2H-tetrazole gave 2'-[2-(1-methyl-1-phenylethyl)-2H-tetrazol-5-yl]biphenyl-4-carbaldehyde as an oil.

proceeding as in Example 8 but replacing 1-(1,1-dimethylethyl)-5-(2-methoxyphenyl)-2H-tetrazole with 5-(2-methoxyphenyl)-1-triphenylmethyl-1H-tetrazole gave 2'-[2-(triphenylmethyl)-2H-tetrazol-5-yl]biphenyl-4-carbaldehyde as an oil.

EXAMPLE 9

2'-[2-(1-Methyl-1-phenylethyl)-2H-tetrazol-5-yl]biphenyl-4-carbaldehyde

The following is the preparation of a protected 2'-(2H-tetrazol-5-yl)biphenyl-4-carbaldehyde wherein the protective group is 1-methyl-1-phenylethyl.

A solution of 1-bromo-4-dimethoxymethylbenzene (2.24 g, 9.7 mmol), prepared as in Example 5, in 20 mL of dry diethyl ether was cooled to between −60° and −65° C. under nitrogen and n-butyllithium (6.3 mL, 1.6 M in hexane, 10.0 mmol) was added over 5 minutes. The reaction mixture was held at −40° C. to −35° C. for 30 minutes and then 5-(2-methoxyphenyl)-1-(1-methyl-1-phenylethyl)-1H-tetrazole (2.4 g, 8.01 mmol), prepared as in Example 6, in 5.0 mL of diethyl ether was added. The mixture was allowed to warm to room temperature and then stirred for 2 hours. The reaction was quenched with saturated ammonium chloride and extracted with ethyl acetate and concentrated. Purification by column chromatography on silica gel (elution: 10% ethyl acetate in hexane) gave 4-dimethoxymethyl-2'-[2-(1-methyl-1-phenylethyl)-2H-tetrazol-5-yl]biphenyl as an oil.

A solution of 4-dimethoxymethyl-2'-[2-(1-methyl-1-phenylethyl)-2H-tetrazol-5-yl]biphenyl (2.9 g, 7.0 mmol) and 15 mL of 4 M hydrochloric acid in 50 mL of methanol was stirred at room temperature for 18 hours. The mixture was diluted with 200 mL of diethyl acetate and poured into 300 mL of water. The ethyl acetate layer was washed 3 times with water, dried over magnesium sulfate and concentrated giving a white, waxy solid (2.51 g). A portion of the solid (1.53 g) was crystallized from diethyl ether and isolated. Drying gave 2'-[2-(1-methyl-1-phenylethyl)-2H-tetrazol-5-yl]biphenyl-4-carbaldehyde (1.2 g, 3.2 mmol), m.p. 98.5°-97° C.

EXAMPLE 10

2'-[2-(1-Methyl-1-phenylethyl)-2H-tetrazol-5-yl]biphenyl-4-methanol

The following is the preparation of a protected 2'-(2H-tetrazol-5-yl)-biphenyl-4-methanol wherein the protective group is 1-methyl-1-phenylethyl.

A solution of lithium aluminum hydride (1.9 L, 1 M in THF) was cooled to −30° C. and 2'-[2-(1-methyl-1-phenylethyl)-2H-tetrazol-5-yl]biphenyl-4-carboxylic acid methyl ester (0.848 kg, 2.13 mol), prepared as in Example 3, in 3.5 L of THF was added at a rate such that the reaction temperature remained below −10° C. The mixture was allowed to warm to 0° C. and 77 mL of water, 77 mL of 15% sodium hydroxide and 230 mL of water were sequentially added. The mixture was filtered and the filter cake washed with 3×500 mL of THF. The filtrate was concentrated, then 4 L of hexanes were added and a crystalline product was obtained. The product was isolated by filtration and the filter cake was washed with hexanes. Drying gave 2'-[2-(1-methyl-1-phenylethyl)-2H-tetrazol-5-yl]-biphenyl-4-methanol (0.788 kg, 2.12 mol), m.p. 117°-120° C.

EXAMPLE 11

2'-[2-(1-Methyl-1-phenylethyl)-2H-tetrazol-5-yl]biphenyl-4-methanol

The following is the preparation of a protected 2'-(2H-tetrazol-5-yl)-biphenyl-4-methanol wherein the protective group is 1-methyl-1-phenylethyl.

A solution of 2,-[2-(1-methyl-1-phenylethyl)-2H-tetrazol-5-yl]biphenyl-4-carbaldehyde (0.62 g, 1.7 mmol), prepared as in Example 8 or 9, and sodium borohydride in 30 mL of absolute ethanol was stirred at room temperature for 1 hour. The mixture poured into 150 mL of water and the mixture was extracted with ethyl acetate. The ethyl acetate layer was dried over magnesium sulfate and then concentrated. The residue was dissolved in approximately 10 mL of absolute diethyl ether and the solution was cooled in an ice bath giving a precipitate. The precipitate was isolated by filtration and drying gave 2'-[2-(1-methyl-1-phenylethyl)-2H-tetrazol-5-yl]biphenyl-4-methanol (0.37 g, 1.0 mmol), m.p. 119°-120° C.

EXAMPLE 12

4-Bromomethyl-2'-[2-(1-methyl-1-phenylethyl)-2H-tetrazol-5-yl]biphenyl

The following is the prepartion of a compound of Formula III in which P is 1-methyl-1-phenylethyl and X is bromo.

A mixture of 2'-[2-(1-methyl-1-phenylethyl)-2H-tetrazol-5-yl]biphenyl-4-methanol (700 g, 1.89 mol), prepared as in Example 10 or 11, and N-bromosuccinimide (420 g, 2.36 mol) in 6 L of THF was cooled to −10° C. Triphenylphosphine (610 g, 2.33 mol) in 2 L THF was added at a rate such that the reaction temperature remained below 30° C. The mixture was cooled to 10° C., 120 mL of methanol was added and a crystalline solid was obtained. The mixture was filtered and the filter cake was washed with 1 L of THF. The filtrate was extracted with 4 L of water and 2.5 L of ethyl acetate and the organic layer was washed with 4 L of water. The organic layer was concentrated to a slurry and L Of methanol was added. The mixture was cooled while stirring for 2 hours and a crystalline product was obtained. The product was isolated by filtration and the filter cake was washed with 1 L of cold methanol. Drying gave 653 g of product.

The mother liquor from the crystalization was concentrated and combined with 1 L of methanol. The mixture was warmed and stirred. The mixture then was cooled and a crystalline product was obtained. The product was isolated by filtration and the filter cake washed with 2×100 mL of cold methanol. Drying gave 111 g of product. Combining the products from each crystallization gave 4-bromomethyl-2'-[2-(1-methyl-1-phenylethyl)-2H-tetrazol-5-yl]biphenyl (0.764 kg, 1.76 mol), m.p. 108°–109° C.

EXAMPLE 13

1-Butylindole-3-carboxylic acid

Sodium hydride (1.80 Kg, 75.0 mol) in DMF was cooled to approximately 5° C. and a solution of indole 4.36 Kg, 37.2 mol) in DMF was added at a rate such that the evolving hydrogen gas is kept under control. The mixture was cooled to 5° C. and then n-butylbromide (5.35 Kg, 4.2 L, 39.1 mol) was added. The mixture was stirred for approximately 60 minutes, cooled to 5° C. and then trifluoroacetic anhydride (8.84 Kg, 5.95 L, 37.2 mol) was added. This mixture was stirred for approximately 60 minutes and then 110 mL of water was added. This mixture was stirred for approximately 6 hours. Filtration gave crude 1-butyl-3-trifluoroacetylindole (12.5 kg).

A solution of potassium hydroxide (6.9 kg, 133.7 mol) in 14 mL of methanol was heated to reflux temperature and crude 1-butyl-3-trifluoroacetylindole (11.5 kg) in 35 L of toluene was added slowly. The mixture was heated under reflux for 60 minutes, cooled to approximately 50° C. and 80 L of water was added. The aqueous layer was separated and extracted with 30 L toluene. Phosphoric acid was then added to the aqueous layer until a pH of 7.16 was obtained. Ethyl acetate was then added, followed by additional phosphoric acid until a pH of 2.38 was obtained. The ethyl acetate layer was separated and washed twice with water (2×40 L). The ethyl acetate layer was filtered, heated to 83° C. and combined with 40 L of heptane at which point crystallization occured. The mixture distilled until the mixture heated to 89° C., after which the mixture was cooled slowly. A crystalline product was obtained and isolated by filtration. Drying under nitrogen gave 1-butylindole-3-carboxylic acid (6.64 kg, 30.6 mol), m.p. 124°–126° C.

EXAMPLE 14

1-Butyl-2-{2'-[2-(1-methyl-1-phenylethyl)-2H-tetrazol-5-yl]biphenyl-4-ylmethyl}-1H-indole-3-carboxylic acid The following is the preparation of protected 1-butyl-2'-(2H-tetrazol-5-yl)biphenyl-4-ylmethyl]-1H-indole-3-carboxylic acid wherein the protective group is 1-methyl-1-phenylethyl.

A solution of 1-butyl-3-indolecarboxylic acid (20.0 g, 0.092 mol), prepared as Example 13, in 450 mL of THF was cooled to −40° C. under argon. n-Butyllithium (2.5 M in hexane, 73.7 mL, 0.184 mol) was added at a rate such that the reaction temperature remained below −25° C. and then the mixture was allowed to warm to 0° C. The mixture was let stand for 30 minutes, cooled to −40° C. and then zinc chloride (1 M in diethyl ether, 220 mL, 0.219 mol), tetrakis(triphenylphosphine)palladium(0) (2.03 g, 0.0018 mol) and 4-bromomethyl-2'-[2-(1-methyl-1-phenylethyl)-2H-tetrazol-5-yl]biphenyl (38.01 g, 0.0878 mol), prepared as in Example 12, were sequencially added. The mixture was allowed to warm to room temperature and then 200 mL of ethyl acetate and 200 mL of 1N sodium hydroxide were added. The aqueous layer was separated and extracted with 50 mL of ethyl acetate. The combined ethyl acetate layers were washed with 200 mL of 1 M hydrochloric acid and then brine and dried (sodium sulfate). The mixture was filtered and the solvent was removed. The residue was redissolved in 200 mL of ethyl acetate and 200 mL of methanol was slowly added to the solution giving a crystalline product which was isolated by filtration. The filtrate was concentrated and the residue was dissolved in 50 mL of ethyl acetate and proceeding similarly additional crystalline product was obtained. Drying and combining the products from each crystallization gave 1-butyl-2-{2'-[2-(1-methyl-1-phenylethyl)-2H-tetrazol-5-yl]biphenyl-4-ylmethyl}1H-indole-3-carboxylic acid (45.5 g, 0.08 mol), m.p. 146'–148° C.

EXAMPLE 15

1-Butyl-2-[2-(2H-tetrazol-5-yl)biphenyl-4-ylmethyl]-1H-indole-3-carboxylic Acid

A mixture of 1-butyl-2-{2'-[2-(1-methyl-1-phenyl)-2H-tetrazol-5-yl]-biphenyl-4-ylmethyl}-1H-indole-3-carboxylic acid (8.0 g, 0.0141 mol), prepared as in Example 14, pentaerythritol tetrakis(2-mercaptoacetate) (4.84 mL, 0.0155 mol) and boron trifluoride etherate (6.92 mL, 0.056 mol) in 120 mL of acetonitrile was stirred at room temperature for 1.5 hours. The reaction mixture was partitioned between 180 mL of 1 M sodium hydroxide and 40 mL of ethyl acetate. The sodium hydroxide layer was stirred and 3 M hydrochloric acid was added giving a crystalline product. The product was isolated by filtration and the filter cake was washed 3 times with 30 mL each of methanol. Drying gave 1-butyl-2-[2'-(2H-tetrazol-5-yl)biphenyl-4-ylmethyl]-1H-indole-3-carboxylic acid (5.9 g, 0.0131 mol), m.p. 228°–230° C. dec.

We claim:

1. A process for the preparation of 1-butyl-2-[2'-(2H-tetrazol-5-yl)-biphenyl-4-ylmethyl]-1H-indole-3-carboxylic acid which process comprises:

(A)

(i) treating protected 5-phenyl-2H-tetrazole with an organometallic base to give ortho-metalated protected 5-phenyl-2H-tetrazole, (ii) optionally treating the ortho-metalated protected 5-phenyl-2H-tetrazole with a metal halide to give ortho-transmetalated protected 5-phenyl-2H-tetrazole, (iii) reacting the ortho-metalated or ortho-transmetalated protected 5-phenyl-2H-tetrazole, optionally in the presence of phosphinated nickel or palladium catalyst, with a compound of Formula II:

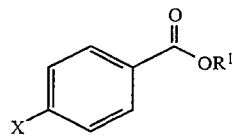

in which X is halo and $R^1$ is $(C_{1-4})$alkyl, to give protected 2'- (2H-tetrazol-5-yl) biphenyl-4-carboxylic acid $(C_{1-4})$ alkyl ester, (iv) reducing the protected 2'- (2H-tetrazol-5-yl)biphenyl-4-carboxylic acid $(C_{1-4})$alkyl ester to give protected 2'-(2H-tetrazol-5-yl)biphenyl-4-methanol, and (v) halogenating the protected 2'-(2H-tetrazol-5-yl)biphenyl-4-methanol to give protected 4-halomethyl-2'- (2H-tetrazol-5-yl) biphenyl;

(B) reacting the protected 4-halomethyl-2'-(2H-tetrazol-5-yl)biphenyl, optionally in the presence of phosphinated nickel or palladium catalyst, with 2-metalated or 2-transmetalated 1-but-1-yl-1H-indole-3-carboxylic acid to give protected 1-butyl-2-[2'-(2H-tetrazol-5-yl)biphenyl-4-ylmethyl]-1H-indole-3-carboxylic acid; and (C) deprotecting.

2. The process of claim 1 which comprises:
(A)
(i) treating 2-(1-methyl- 1-phenylethyl)-5-phenyl-2H-tetrazole with n-butyllithium to give ortholithiated 2-(1-methyl-1-phenylethyl)-5-phenyl-2H-tetrazole, (ii) treating the ortho-lithiated 2-(1-methyl-1-phenylethyl)-5-phenyl-2H-tetrazole with a metal halide selected from zinc chloride, magnesium chloride or nickel chloride to give ortho-transmetalated 2-(1-methyl-1-phenylethyl)-5-phenyl-2H-tetrazole, (iii) reacting the ortho-transmetalated 2-(1-methyl-1-phenylethyl)-5-phenyl-2H-tetrazole with methyl 4-bromobenzoate in the presence of phosphinated nickel catalyst to give 2'-[2-(1-methyl-1-phenylethyl)-2H-tetrazol-5-yl]biphenyl-4-carboxylic acid methyl ester, (iv) reducing the 2'-[2-(1-methyl-1-phenylethyl)-2H-tetrazol-5-yl]-biphenyl-4-carboxylic acid methyl ester to give 2'-[2-(1-methyl-1-phenylethyl)-2H-tetrazol-5-yl]biphenyl-4-methanol and (v) brominating the 2'-[2-(1-methyl-1-phenylethyl)-2H-tetrazol-5-yl]biphenyl-4-methanol to give 4-bromomethyl-2'-[2-(1-methyl-1-phenylethyl)-2H-tetrazol-5 -yl]biphenyl;

(B) reacting the 4-bromomethyl-2'-[2-(1-methyl-1-phenylethyl)-2H-tetrazol-5 -yl]biphenyl with 2-transmetalated 1-butyl-1H-indole-3-carboxylic acid in the presence of phosphinated palladium catalyst to give 1-butyl-2'-[2-( 1 -methyl-1 -phenylethyl )-2H-tetrazol-5-yl]biphenyl-4 -ylmethyl]-3-carboxylic acid; and (C) deprotecting.

3. The process of claim 2 in which the metal halide is zinc chloride, the phosphinated nickel catalyst is bis(triphenylphosphine)nickel(II)chloride, the 2-transmetalated 1-butyl-1H-indole-3-carboxylic acid is 1-butyl-3-carboxy-1H-indol-2-ylzinc chloride, 1-butyl-3-carboxy-1H-indol-2-ylmagnesium chloride or 1-butyl-3-carboxy-1H-indol-2-ylnickel chloride and the phosphinated palladium catalyst is tetrakis(triphenylphosphine)palladium(0).

4. The process of claim 3 in which the 2-transmetalated 1-butyl-1H-indole-3-carboxylic acid is 1-butyl-3-carboxy-1H-indol-2-ylzinc chloride.

5. The process of claim 4 in which deprotecting comprises reacting the 1-butyl-2-[2'-(2-(1-methyl-1-phenylethyl)-2H-tetrazol-5yl)biphenyl-4-methyl]-1H-indole-3-carboxylic acid with a Lewis acid in the presence of a thiol.

6. The process of claim 5 in which the Lewis acid is boron trifluoride etherate, tin(IV) chloride, titanium-(IV) chloride, titanium(III)chloride, zinc chloride or selenium(IV) chloride and the thiol is methyl thioglycolate, pentaerythritol tetrakis(2-mercaptoacetate), $(C_{1-4})$alkanethiol, arylthiol, 2-mercaptoacetic acid or $(C_{1-4})$alkyl 2-mercaptoacetate.

7. The process of claim 6 in which the Lewis acid is boron trifluoride etherate and the thiol is methyl thioglycolate or pentaerythritol tetrakis(2-mercaptoacetate).

8. A process for the preparation of 1-butyl-2-[2'-(2H-tetrazol-5-yl)-biphenyl-4-ylmethyl]-1H-indole-3-carboxylic acid which process comprises:
(A)
(i) treating 1-butyl-1H-indole-3-carboxylic acid with an organometallic base to give 2-metalated 1-butyl-1H-indole-3-carboxylic acid, acid with a metal halide to give 2-transmetalated 1-butyl-1H-indole-3-carboxylic acid and (iii) reacting the 2-metalated or 2-transmetalated 1-butyl-1H-indole-3-carboxylic acid, optionally in the presence of phosphinated nickel or palladium catalyst, with protected 4-halomethyl-2'-(2H-tetrazol-5-yl)biphenyl to give protected 1-butyl-2-[2'-(2H-tetrazol-5-yl)biphenyl-4-ylmethyl]-1H-indole-3-carboxylic acid and (B) deprotecting.

9. The process of claim 8 which comprises:
(A)
(i) treating 1-butyl-1H-indole-3-carboxylic acid with n-butyllithium to give 2-lithiated 1-butyl-1H-indole-3-carboxylic acid, (ii) treating the 2-lithiated 1-butyl-1H-indole-3-carboxylic acid with a metal halide selected from zinc chloride, magnesium chloride or nickel chloride to give 2-transmetalated 1-butyl-1H-indole-3-carboxylic acid and (iii) reacting the 2-transmetalated 1-butyl-1H-indole-3-carboxylic acid with 4-bromomethyl-2'-[2-(1-methyl-1-phenylethyl)-2H-tetrazol-5-yl]biphenyl in the presence of phosphinated palladium catalyst to give 1-butyl-2-{2'-[2-(1-methyl-1-phenylethyl)-2H-tetrazol-5-yl]biphenyl-4-ylmethyl}-1H-indole-3-carboxylic acid and (B) deprotecting.

10. The process of claim 9 in which the metal halide is selected from zinc chloride and the catalyst is tetrakis(triphenylphosphine)palladium(O).

11. The process of claim 10 in which deprotecting comprises reacting the 1-butyl-2-[2'-(2-(1-methyl-1-phenylethyl)2H-tetrazol-5-yl)biphenyl-4-ylmethyl]-1H-indole-3-carboxylic acid with a Lewis acid in the presence of a thiol.

12. The process of claim 11 in which the Lewis acid is boron trifluoride etherate, tin(IV) chloride, titanium(IV) chloride, titanium(III)chloride, zinc chloride or selenium(IV) chloride and the thiol is methyl thioglycolate, pentaerythritol tetrakis(2-mercaptoacetate), ($C_{1-4}$)alkanethiol, arylthiol, 2-mercaptoacetic acid or ($C_{1-4}$)alkyl 2-mercaptoacetate.

13. The process of claim 12 in which the Lewis acid is boron trifluoride etherate and the thiol is methyl thioglycolate or pentaerythritol tetrakis(2-mercaptoacetate).

* * * * *

UNITED STATES PATENT AND TRADEMARK OFFICE
CERTIFICATE OF CORRECTION

PATENT NO. : 5,412,102
DATED : May 2, 1995
INVENTOR(S) : Clark, et al.

It is certified that error appears in the above-identified patent and that said Letters Patent is hereby corrected as shown below:

Claim 2, at column 19, line 67, after "biphenyl-4-ylmethyl]" and before "-3-carboxylic acid;" insert --1H-indole--.

Claim 5, at column 20, line 16, after "biphenyl-4-" and before "methyl]" insert --yl--.

Claim 8, at column 20, line 37, after "-3-carboxylic acid," and before "acid with a metal halide" insert --(ii) optionally treating the 2-metalated 1-butyl-1H-indole-3-carboxylic--.

Claim 11, at column 21, line 3, after "phenylethyl)" and before "2H-tetrazol" insert a hyphen.

Signed and Sealed this

Fifth Day of September, 1995

Attest:

BRUCE LEHMAN

*Attesting Officer*                *Commissioner of Patents and Trademarks*